(12) United States Patent
Cohen

(10) Patent No.: US 7,999,147 B2
(45) Date of Patent: Aug. 16, 2011

(54) REDUCTION OF ODORS IN ABSORBENT ARTICLES

(75) Inventor: Richmond R. Cohen, Williamsport, PA (US)

(73) Assignee: First Quality Products, Inc., Great Neck, NY (US)

(*) Notice: Subject to any disclaimer, the term of this patent is extended or adjusted under 35 U.S.C. 154(b) by 430 days.

(21) Appl. No.: 11/508,100

(22) Filed: Aug. 22, 2006

(65) Prior Publication Data

US 2006/0282050 A1    Dec. 14, 2006

Related U.S. Application Data

(62) Division of application No. 10/909,929, filed on Aug. 2, 2004, now Pat. No. 7,834,233.

(51) Int. Cl.
*A61F 13/15* (2006.01)
*A61F 13/20* (2006.01)

(52) U.S. Cl. ........ 604/359; 604/360; 604/367; 427/180; 427/421.1

(58) Field of Classification Search .................. 604/359, 604/360, 367, 368; 424/719, 724
See application file for complete search history.

(56) References Cited

U.S. PATENT DOCUMENTS 4,448,916 A * 5/1984 Martenson .................... 524/106
5,733,272 A * 3/1998 Brunner et al. ............... 604/359

FOREIGN PATENT DOCUMENTS

| EP | 1034799 A1 * | 9/2000 |
| EP | 1034804 A1 * | 9/2000 |
| WO | 03039401 A2 | 5/2003 |

OTHER PUBLICATIONS

Supplementary European Search Report, dated Aug. 2, 2010.

* cited by examiner

*Primary Examiner* — Melanie J Hand
(74) *Attorney, Agent, or Firm* — Amster, Rothstein & Ebenstein LLP

(57) ABSTRACT

Provided are absorbent articles for retaining a malodorous bodily fluid. The absorbent articles comprise an additive that is a quaternary ammonium salt that is water soluble at 37° C., comprises an alkyl $C_{16}$-$C_{21}$ chain, and contains at least two oxygen atoms in the anionic portion of the salt. Also provided are methods of preparing absorbent articles, including disposable absorbent articles, containing the above additive.

9 Claims, No Drawings

REDUCTION OF ODORS IN ABSORBENT ARTICLES

CROSS-REFERENCE TO RELATED APPLICATION

This application is a divisional of prior application Ser. No. 10/909,929, filed Aug. 2, 2004 now U.S. Pat. No. 7,834,233.

BACKGROUND (1) Field of the Invention

The present invention generally relates to compositions and methods for reducing odors in absorbent articles. More specifically, the invention is directed to the use of particular compounds in absorbent articles for reducing odors from bodily fluids absorbed in the articles.

(2) Description of the Related Art

References Cited

Baker, L., "An Ounce of Prevention . . . A New Approach to Odor Control for Adult Incontinence", INSIGHT 2001 Absorbent Products Conference, October 2001.

Smith, J., Wheeler, E., Weiss, R., "Monitoring Ammonia Levels in Livestock Housing", Herd Health Memo, November 1999.

U.S. Pat. No. 6,376,741 B1.
U.S. Pat. No. 6,369,290 B1.
U.S. Pat. No. 6,342,653.
U.S. Pat. No. 6,229,062 B1.
U.S. Pat. No. 5,769,832.
U.S. Pat. No. 5,733,272.
U.S. Pat. No. 5,591,146.
U.S. Pat. No. 5,429,628.
U.S. Pat. No. 5,103,500.
U.S. Pat. No. 5,079,004.
U.S. Pat. No. 5,037,412.
U.S. Pat. No. 4,842,593.
U.S. Pat. No. 4,059,114.
U.S. Pat. No. 3,920,020.
U.S. Pat. No. 3,691,271.
U.S. Statutory Invention Registration H1,732.

The malodorous gases emanating from used absorbent hygiene articles can be unhealthful and unpleasant to inhale and could be a source of embarrassment to the wearer. Discreetness is a desirable characteristic of an absorbent article to an adult, and part of that discreetness includes the elimination of malodors from the used article. Reduction of the longer-term malodors emanating from the vicinity of the area of disposal of the soiled articles, either in the home or in the institution, is also needed.

It is known that several gases contribute to the malodor resulting from the breakdown of human exudates, such as urine, feces or menses. Of these gases, ammonia is considered to be one of the most potent and recognizable odors associated with aged human exudates, although there are other gases including those of organic acids and sulfur-containing compounds that contribute to malodor. Many prior efforts to diminish malodor from used absorbent articles have focused on reducing ammonia. Ammonia is widely believed to contribute to diaper dermatitis, also known as diaper rash.

Ammonia is produced by the breakdown of urea from urine. Certain bacteria, in the presence of the enzyme urease, digest the urea and produce carbon dioxide and ammonia. But as the bacteria reproduce, more urea is digested, and the malodor (ammonia production) increases with time. It takes hours for ammonia to be produced in significant quantities according to this degradation process. Other odors emanating from urine or waste may be detectable immediately or after short times.

There have been numerous attempts to prevent malodor from used diapers. One category of such attempts involves masking. With masking, another more pleasant odor, such as a perfume, is introduced in such quantities as to overpower the malodor. See, e.g., U.S. Pat. No. 5,769,832. Such methods do not reduce ammonia production, so even if effective masking occurs, the unhealthful inhalation of ammonia gas would continue, and the harmful impact on skin would not be diminished.

Other techniques to reduce odor involve adsorption or absorption. For example, superabsorbent polymer, molecular sieves, activated charcoal, and silica have been used as odor control agents. See, e.g., U.S. Pat. No. 6,376,741 B1. Malodor can also be reduced by eliminating or delaying ammonia production. Included in such methods are agents which act as urease inhibitors, such as sodium tetraborate pentahydrate (U.S. Pat. No. 6,342,653). Methods involving the use of weak acids such as citric acid to lower the pH of the absorbents in the diaper have also been tried. A more acidic pH is known to retard the degradation rate of urea. In addition, sodium bicarbonate has been used to inhibit odors from malodorous organic acids (U.S. Pat. No. 5,037,412). Other methods to reduce ammonia production use antimicrobial agents against bacteria, some in conjunction with lower pH (Baker, 2001). Certain quaternary ammonium compounds are examples of such antimicrobials, which have been used to counter ammonia production from urine (U.S. Pat. No. 4,842,593).

Other publications describing treatment of bodily malodors include U.S. Pat. Nos. 6,369,290 B1; 5,733,272; 5,429,628; 6,229,062 B1; 5,591,146; 5,103,500; 5,079,004; 4,059,114; 3,920,020; and 3,691,271; and US Statutory Invention Registration H1,732.

All of the above-described attempts to reduce malodor have demonstrated limited efficacy or have raised other health or environmental issues or concerns. Hence, there is a need for treatments for absorbent articles such as diapers that allow the articles to be effective in reducing the malodor of bodily fluids exposed thereto, and which are safe to wear and are not unhealthy to the general public. Ideally, the treatment removes odors from the soiled article quickly and should also reduce the odors created over longer periods of time, such as that of ammonia.

SUMMARY OF THE INVENTION

Accordingly, the inventor has identified a class of quaternary ammonium compounds that are effective in reducing a malodor of bodily fluids. These compounds are useful in absorbent articles, including diapers.

Thus, in some embodiments, the invention is directed to absorbent articles for retaining a malodorous bodily fluid. The absorbent articles comprise an additive in an amount effective to reduce the malodor of the bodily fluid. In these embodiments, the additive is a quaternary ammonium salt that is water soluble at 37° C., comprises an alkyl $C_{16}$-$C_{21}$ chain, and contains at least two oxygen atoms in the anionic portion of the salt.

In other embodiments, the invention is directed to methods of making an absorbent disposable article. The methods comprise combining a liquid pervious topsheet, a liquid impervious backsheet, an absorbent core, and an additive present in an amount effective to reduce a malodor of a bodily fluid, such that the article may be worn by a human in a manner allowing the article to absorb and retain a bodily fluid. The additive in these embodiments is a quaternary ammonium salt that is water soluble at 37° C., comprises a $C_{16}$-$C_{21}$ chain, and contains at least two oxygen atoms in the anionic portion of the salt.

The present invention is also directed to additional methods of making an absorbent disposable article. The methods comprise obtaining an absorbent core comprising an additive, and combining a liquid pervious topsheet, a liquid impervious backsheet, and the absorbent core such that the article may be worn by a human in a manner allowing the article to absorb and retain a bodily fluid. As in embodiments described above, the additive is a quaternary ammonium salt that is water soluble at 37° C., comprises a $C_{16}$-$C_{21}$ chain, and contains at least two oxygen atoms in the anionic portion of the salt.

The invention is additionally directed to methods of preparing an absorbent article. The methods comprise treating the absorbent article with an additive in an amount effective to reduce the malodor of a bodily fluid later absorbed by the absorbent article. As in embodiments described above, the additive is a quaternary ammonium salt that is water soluble at 37° C., comprises a $C_{16}$-$C_{21}$ chain, and contains at least two oxygen atoms in the anionic portion of the salt.

DETAILED DESCRIPTION OF THE INVENTION

The inventor has discovered that various quaternary ammonium compounds are effective in reducing various malodors from bodily fluids when incorporated into an absorbent article. The compounds are quaternary ammonium salts that are water soluble at 37° C., comprise an alkyl $C_{16}$-$C_{21}$ chain, and contain at least two oxygen atoms in the anionic portion of the salt. Without being bound by any specific mechanism, it is believed that these compounds are unexpectedly effective in binding to compounds that contribute to the malodor, for example ammonia.

Thus, in some embodiments, the invention is directed to absorbent articles for retaining a malodorous bodily fluid. The absorbent articles comprise an additive in an amount effective to reduce the malodor of the bodily fluid. The additive is a quaternary ammonium salt that is water soluble at 37° C., comprises an alkyl $C_{16}$-$C_{21}$ chain, and contains at least two oxygen atoms in the anionic portion of the salt. Absorbent articles comprising the additive exhibit a consistent reduction in the concentration of ammonia and other malodorous materials from a used absorbent article, when compared to articles without the additive. Furthermore, articles of the invention achieve these odor reduction characteristics without using an excessive, uneconomical quantity of the additive. Additionally, several compounds that meet the criteria of the additives are commercially available. Finally, the treated article reduces malodor immediately and for an enduring period of time.

In preferred embodiments, the additive has Formula I

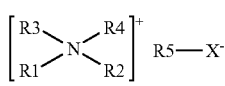

Formula I where R1, R2, R3, R4 and R5 are independently a straight or branched $C_1$-$C_{21}$ alkyl, alkenyl, alkynyl, haloalkyl, alkylaryl, arylalkyl, alkoxy, alkoxyalkyl, dialkylamino, dialkylamido, alkylthio, (polyalkyl)aryl, cycloalkyl or an N- or O-containing ring, optionally further comprising an N, O or S, where one of R1, R2, R3 or R4 comprises an alkyl $C_{16}$-$C_{21}$ chain and wherein any two of R1, R2, R3 or R4 may be joined to form a ring; and X is $OSO_3$, ONO, $OCO_2$ or COO. In more preferred embodiments, the moiety having the alkyl $C_{16}$-$C_{21}$ chain is a mixture of alkyl $C_{16}$ and $C_{18}$ chains, e.g., as occurs in soya derivatives. In other more preferred embodiments, X is $OSO_3$; in additional preferred embodiments, R5 is a methyl group or an ethyl group.

In even more preferred embodiments, the additive has Formula II

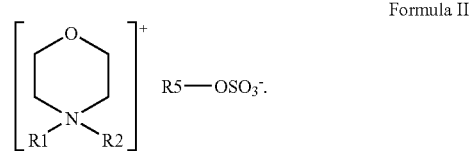

Formula II

Preferably, R1 is a mixture of alkyl $C_{16}$ and $C_{18}$ chains in the Formula II additives; and/or R5 is a methyl group or an ethyl group.

In the most preferred embodiments, the additive has one of the following formulas:

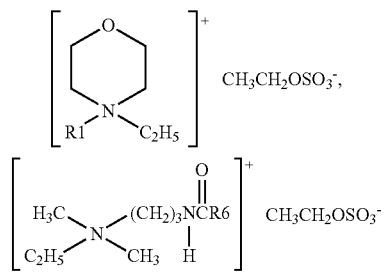

wherein R6 comprises an alkyl $C_{16}$-$C_{21}$ chain,

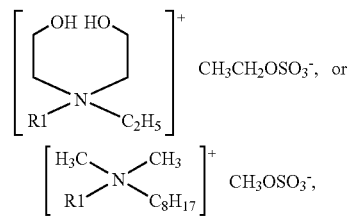

preferably where R1 or R6 is a mixture of alkyl $C_{16}$ and $C_{18}$ chains. Examples of these most preferred compounds were utilized in experiments described in the Examples, and include 4-ethyl-4-soya morpholinium ethyl sulfate (FORESTALL); ethylbis(hydroxyethyl)tallowalkyl ammonium ethyl sulfate; hydrogenated tallowalkyl(2-ethylhexyl) dimethylammonium methyl sulfate (ARQUAD® HTL8-MS); and 1-propanaminium, 3-amino-N-ethyl-N,N-dimethyl-N-soya acyl derivative, ethyl sulfate.

The quantity of the active agent in an absorbent article of the invention may range from 0.001-10 wt. % of the absorbent material. Preferably, the quantity of the active agent in the absorbent material ranges from about 0.01-3 wt. %, most preferably from about 0.05-1 wt. % of the absorbent material in the article.

The present invention includes any absorbent article useful for absorbing bodily fluids, including disposable wipes, bibs, underpads, underwear, socks, swimwear, tissue, and, preferably, diapers, incontinence pads, pantiliners, sanitary napkins, wipes, and perspiration pads.

In some preferred embodiments, the article is disposable. Examples of such disposable articles include incontinence pads, pantiliners, sanitary napkins, or, most preferably, diapers. Common disposable articles within the scope of the invention comprise a liquid pervious topsheet, a liquid impervious backsheet, and an absorbent core. The additive may be in the topsheet, or, more preferably, in the absorbent core, where most of the absorbed waste, such as urine, is contained after the article is used. Typical absorbent cores comprise cellulose fluff pulp fibers mixed with superabsorbent powder (SAP); in some preferred embodiments, the additive is in the SAP.

The invention is not limited to any particular SAP. Common SAPs are partially cross-linked, polymerized salts of organic acids, such as polyacrylic acids. These bear carboxyl groups, a fraction of which remain free acids and the remaining fraction is neutralized, usually with sodium or potassium counterions. SAPs generally are 25% to 90% neutralized, with the more commonly used SAP materials being about 65% to 80% neutralized. SAPs having this level of neutralization tend to have a pH value of about 6.0. For neutralization less than about 65%, the SAP may bear a lower pH. A desirable pH for low pH SAP is 5.0-5.5. The preferred neutralization range for such a low pH SAP is about 50% to 65%.

In other embodiments of disposable articles of the invention, the additive is in the topsheet. Additionally, the disposable article may also comprise a liquid distribution layer, which may contain the additive.

The most preferred disposable article comprises the additive having the formula

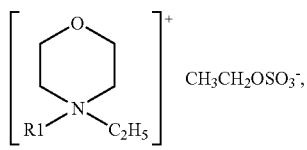

where R1 is a mixture of alkyl $C_{16}$ and $C_{18}$ chains; most preferably, the article is a diaper.

Any of the above-described articles can further comprise at least one additional compound known in the art that reduces odors. Any odor-reducing compound, now known or later discovered, can be added to the articles of the invention. Non-limiting examples of such compounds include compounds that effect pH reduction of one or more of the components in the absorbent structure such as the absorbent core (e.g., an acid or a low pH buffer); addition of fragrances; addition of adsorbents such as molecular sieves, silica, activated charcoal, or sodium bicarbonate; chelating agents such as disodium EDTA, and antimicrobials.

In additional embodiments, the invention is directed to methods of making an absorbent disposable article. The methods comprise combining a liquid pervious topsheet, a liquid impervious backsheet, an absorbent core, and an additive present in an amount effective to reduce a malodor of a bodily fluid, such that the article may be worn by a human in a manner allowing the article to absorb and retain a bodily fluid. In these embodiments, the additive is a quaternary ammonium salt that is water soluble at 37° C. and comprises a $C_{16}$-$C_{21}$ chain and contains at least two oxygen atoms in the anionic portion of the salt, as described in the context of the absorbent article embodiments described above.

As in previously described embodiments, the additive preferably has Formula I

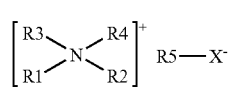

Formula I where R1, R2, R3, R4 and R5 are independently a straight or branched $C_1$-$C_{21}$ alkyl, alkenyl, alkynyl, haloalkyl, alkylaryl, arylalkyl, alkoxy, alkoxyalkyl, dialkylamino, dialkylamido, alkylthio, (polyalkyl)aryl, cycloalkyl or an N- or O-containing ring, optionally further comprising an N, O or S, where one of R1, R2, R3 or R4 comprises an alkyl $C_{16}$-$C_{21}$ chain and where any two of R1, R2, R3 or R4 may be joined to form a ring; and X is $OSO_3$, ONO, $OCO_2$ or COO. Also as described above, the moiety having the alkyl $C_{16}$-$C_{21}$ chain is more preferably a mixture of alkyl $C_{16}$ and $C_{18}$ chains; X is more preferably $OSO_3$; and R5 is more preferably a methyl group or an ethyl group. In the most preferred embodiments, the additive has one of the following formulas:

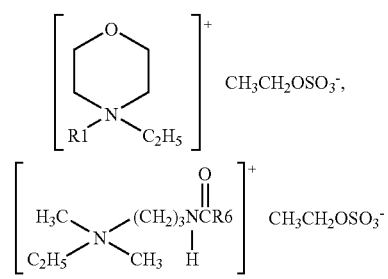

wherein R6 comprises an alkyl $C_{16}$-$C_{21}$ chain,

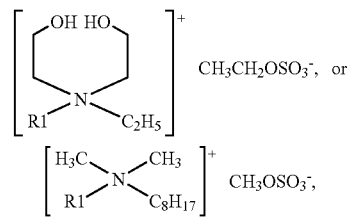

where R1 or R6 is preferably a mixture of alkyl $C_{16}$ and $C_{18}$ chains. The disposable article of these embodiments is most preferably a diaper; the additive most preferable for these diapers is

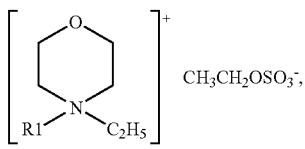

where R1 is a mixture of alkyl $C_{16}$ and $C_{18}$ chains.

The additive may be sprayed, immersed, wiped or otherwise contacted with a component of the disposable article during its manufacture. The additive can also be carried in a dry form and can be applied to the component by an appropriate means, such as gravimetric dosing of a powder. The additive may also be microencapsulated or immobilized by some other means and applied to the absorbent article. Furthermore, the additive may be added at any stage of the article's manufacture, or it may be incorporated within one of the raw materials used in the absorbent article such as the fluff pulp, superabsorbent powder (SAP), acquisition layer, topsheet, or other material contacting the exudates. Of these, the preferred materials in which to incorporate the active agent are the SAP and the fluff pulp, with the most preferred being the SAP.

The disposable article of these embodiments may be manufactured in any manner known. A conventional method includes the use of a hammermill. In a preferred method, the additive is sprayed continuously or intermittently to the absorbent core or the pulp board as it enters the hammermill. In the absorbent core, the additive is available to contact the absorbed urine or other malodorous bodily fluid. In a preferred embodiment of the invention, the treatment is targeted in an area of the absorbent core where most of the waste will be contained, such as the crotch area of a diaper. In these embodiments, the water from the spray is either dried from the heat in the hammermill or dried through the application of heat or through evaporation, and the article is used by the wearer as normal. In another preferred embodiment of the invention, the raw materials of the absorbent article such as the fluff pulp board and/or the SAP contain effective quantities of the additive prepared offline and then are used in the manufacturing of an absorbent article of the invention.

In other embodiments, the additive may be contacted with the topsheet.

Some disposable articles also comprise a liquid distribution layer that is generally incorporated into the article during its manufacture. In some embodiments, the additive may be contacted with the liquid distribution layer.

The methods of making the disposable article may further comprise addition to the article of at least one additional compound that reduces odors. Any odor-reducing compound, now known or later discovered, can be added to the articles of the invention. Non-limiting examples of such compounds include compounds that effect pH reduction of one or more of the components in the absorbent structure such as the absorbent core (e.g., an acid or a low pH buffer); addition of fragrances; addition of adsorbents such as molecular sieves, silica, activated charcoal, or sodium bicarbonate; chelating agents such as disodium EDTA, and antimicrobials.

As discussed above, the additive may be previously added to an absorbent core or a component of the absorbent core, then the absorbent core-additive combination is used in the manufacture of the article. Thus, in additional embodiments, the invention is directed to methods of making an absorbent disposable article, the methods comprise obtaining an absorbent core comprising an additive, and combining a liquid pervious topsheet, a liquid impervious backsheet, and the absorbent core such that the article may be worn by a human in a manner allowing the article to absorb and retain a bodily fluid. As in the embodiments discussed above, the additive in these embodiments is a quaternary ammonium salt that is water soluble at 37° C., comprises a $C_{16}$-$C_{21}$ chain, and contains at least two oxygen atoms in the anionic portion of the salt.

In preferred embodiments, the absorbent core comprises cellulose fluff pulp fibers mixed with a superabsorbent powder (SAP), where the additive is in at least one of the cellulose fluff pulp fibers and the SAP.

As with embodiments described above, the additive preferably has Formula I

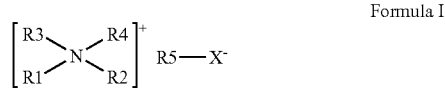

where R1, R2, R3, R4 and R5 are independently a straight or branched $C_1$-$C_{21}$ alkyl, alkenyl, alkynyl, haloalkyl, alkylaryl, arylalkyl, alkoxy, alkoxyalkyl, dialkylamino, dialkylamido, alkylthio, (polyalkyl)aryl, cycloalkyl or an N- or O-containing ring, optionally further comprising an N, O or S, where one of R1, R2, R3 or R4 comprises an alkyl $C_{16}$-$C_{21}$ chain and wherein any two of R1, R2, R3 or R4 may be joined to form a ring; and X is $OSO_3$, $ONO$, $OCO_2$ or $COO$. Most preferably, the additive has one of the following formulas:

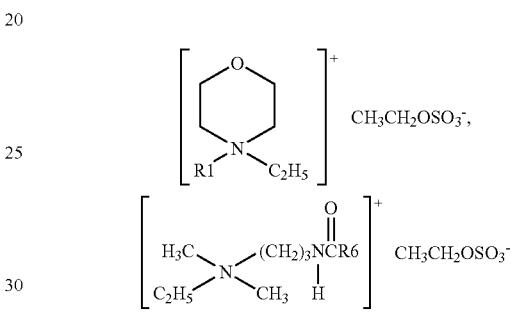

wherein R6 comprises an alkyl $C_{16}$-$C_{21}$ chain,

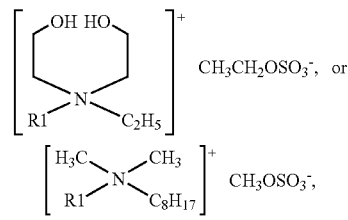

where R1 or R6 is preferably a mixture of alkyl $C_{16}$ and $C_{18}$ chains.

In most preferred embodiments, the disposable article is a diaper. Most preferably, the additive in these diapers has the formula

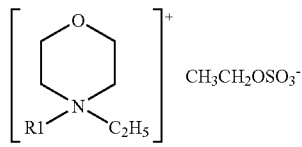

where R1 is a mixture of alkyl $C_{16}$ and $C_{18}$ chains.

In other embodiments, these methods comprise addition to the article of at least one additional compound that reduces odors. Any odor-reducing compound, now known or later discovered, can be added to the articles of the invention. Non-limiting examples of such compounds include compounds that effect pH reduction of one or more of the components in the absorbent structure such as the absorbent core (e.g., an acid or a low pH buffer); addition of fragrances; addition of adsorbents such as molecular sieves, silica, activated charcoal, or sodium bicarbonate; chelating agents such as disodium EDTA, and antimicrobials.

The present invention is also directed to methods of preparing an absorbent article. The methods comprise treating the absorbent article with an additive in an amount effective to reduce the malodor of a bodily fluid later absorbed by the absorbent article. In these embodiments, as in embodiments described above, the additive is a quaternary ammonium salt that is water soluble at 37° C. and comprises a $C_{16}$-$C_{21}$ chain and contains at least two oxygen atoms in the anionic portion of the salt.

In some of these embodiments, the absorbent article is washable and capable of retaining the compound when the compound is added to the absorbent article after washing. Examples of these embodiments include cloth diapers, socks, washable shoes and underwear. In other embodiments, the absorbent article is disposable, as discussed above.

In preferred embodiments, the additive has Formula I

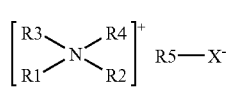

Formula I where R1, R2, R3, R4 and R5 are independently a straight or branched $C_1$-$C_{21}$ alkyl, alkenyl, alkynyl, haloalkyl, alkylaryl, arylalkyl, alkoxy, alkoxyalkyl, dialkylamino, dialkylamido, alkylthio, (polyalkyl)aryl, cycloalkyl or an N- or O-containing ring, optionally further comprising an N, O or S, where one of R1, R2, R3 or R4 comprises an alkyl $C_{16}$-$C_{21}$ chain and wherein any two of R1, R2, R3 or R4 may be joined to form a ring; and X is $OSO_3$, ONO, $OCO_2$ or COO.

In more preferred embodiments, the additive has one of the following formulas:

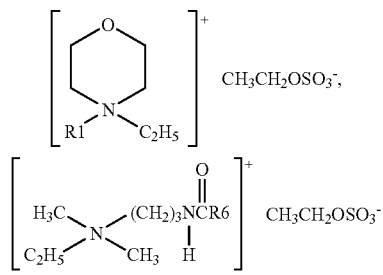

wherein R6 comprises an alkyl $C_{16}$-$C_{21}$ chain,

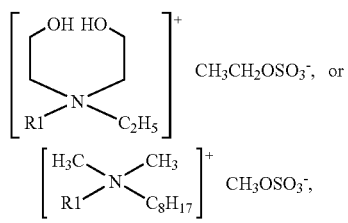

where R1 or R6 is preferably a mixture of alkyl $C_{16}$ and $C_{18}$ chains.

In most preferred embodiments, the additive has the formula

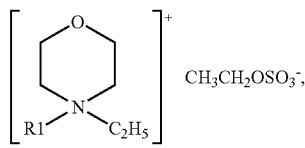

where R1 is a mixture of alkyl $C_{16}$ and $C_{18}$ chains.

The efficacy of the additive for reducing malodor can be determined by any method known in the art, including subjective methods (e.g., surveying responses from people asking which treatment has reduced malodor), or with objective tests (e.g., measuring concentration of ammonia or other malodors in the air around the treated article). Two examples of these tests are as follows. In the first, the concentration of ammonia is measured over time from treated and untreated absorbent compositions containing a urine specimen. In the second test, the level of malodor is judged subjectively between untreated and treated absorbent articles at specific times after they have been soiled. Details of the test procedures are outlined below.

The following is a detailed description of the test method to measure ammonia concentrations. A series of absorbent structures are prepared according to the following. The base absorbent structure is fluff pulp or a combination of fluff and SAP. Then, for example, an aqueous solution is prepared containing a known quantity of a potential treatment for ammonia malodor. An equal quantity of the solution is sprayed onto all but one of the series of absorbent structures. The spraying is applied as uniformly as possible. One absorbent structure is sprayed with an equal volume of water and is the control. All absorbent structures are left out several hours to dry. Each of the absorbent structures is then transferred to Nalgene® Brand 125-ml, narrow-mouth polycarbonate Erlenmeyer flasks. A similar protocol occurs if the treatment is in the form of a solid. Instead of spraying the solid onto the absorbent substrate, the solid is simply manually mixed as uniformly as possible into the absorbent structure.

Straughan® Gastec® ammonia gas dosimeter tubes, grade 3D, are broken off and thereby opened at one end. The declared detection range of the 3D tubes is 25-500 ppm-hr. The open ends of the tubes are forced through the holes in No. 5 one-hole black-rubber stoppers. The tubes are forced through the stoppers to a depth where the entire measuring range of the tubes is visible through the flask. Donors collect a suitable quantity of fresh urine specimen in disposable collection cups marked with volume indications. The specimen is then poured into additional marked cups, one for each flask prepared, and divided into equal volumes. The specimen from each cup is then poured slowly into the open mouth of each flask. The flasks are then sealed tightly with the stoppers, with the open end of the ammonia dosimeter tubes inside the flasks. The date and time are then written on a small label on the flasks.

The flasks are then placed into a water bath set at 37° C. The ammonia dosimeter tubes are checked at discrete time intervals to determine the extent of color change in the reactant within each tube. The original color of the reactant is purple, but in the presence of ammonia, the color changes to yellow. Based on discrete markings on the detector tube, the time-weighted average concentration of ammonia measured in parts per million-hour are read from the scale and recorded. Conversion to a time-weighted average concentration in parts per million requires division by the number of hours the sample has been in the water bath. Readings of ammonia concentrations are read up to 72 hours time or less if any of the concentrations exceed the maximum limit of the detection tube's range.

Using the test method above, additives that are within the scope of the invention will outperform the control and are also expected to maintain a time-weighted average concentration of about 2 ppm or less of ammonia at all times during the experiment. The human detection threshold for odor from ammonia gas varies per individual, ranging from 0.6-50 ppm (Smith et al., 1999), with most people not able to detect ammonia presence at about 2 ppm or less. Hence, we set the limit for efficacy of a treatment of the invention for the time-weighted average concentration of ammonia at about 2 ppm or lower.

The test method for olfactory perception is as follows. An absorbent article is prepared containing an effective amount of the treatment. An identical article, without treatment, is also taken. The articles are labeled with codes unknown to the tester so that the test is done blindly. The tester then donates a suitable quantity of fresh urine specimen in a disposable collection cup marked with volume indications. The specimen is poured into another such cup so that the two cups contain equal volumes of urine. The urine from each cup is poured onto each absorbent article, with the location of the pouring at a position within the target zone of the article. The tester smells the articles immediately and evaluates the odor. Next, the articles are enclosed into plastic Zip-Lock bags. The bags are placed in a convection oven set at 37° C. and incubated for 24 hours. The testers are then asked to open the bags and evaluate the odor. For the treatment to be considered effective, the articles treated with materials within the scope of the invention must be overwhelmingly preferred by the testers.

Preferred embodiments of the invention are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the Examples.

Example 1

Four absorbent structures containing 4.5 g of fluff pulp from grade RAYFLOC® JLD-E, made by Rayonier Inc., and 1.5 g of SAP from grade AQUAKEEP® SA55S, made by Sumitomo Seika Chemicals Co., Ltd. (Japan), are prepared. The first structure is sprayed with 4.5 ml of water and is designated as the control. The other three are sprayed with 4.5 ml of an aqueous solution containing 1% FORESTALL, obtained from Uniqema (Wilmington, Del.). FORESTALL is the tradename for 4-ethyl-4-soya morpholinium ethyl sulfate, an additive that has the chemical characteristics of the invention. The samples are allowed to dry and are then transferred to 125-ml Erlenmeyer flasks.

A healthy human donor provides about 150-250 ml of fresh urine in a collection cup. The urine is divided into four equal volumes and is then distributed equally to each of the four samples. The flasks are then sealed with the stopper/detection tube assembly and placed in the water bath set at 37° C.

Table 1 contains the data measured for three different donors. In the table, the sample designations starting with C refer to the control, and the designations starting with T refer to the treatment described above. The letters X, Y or Z refer to the donor. The numbers in the designation refer to the replicate of the treated samples.

TABLE 1

| | Ammonia Concentration ppm-hour | | | |
|---|---|---|---|---|
| | 8 hour reading | 24 hour reading | 32 hour reading | 48 hour reading |
| C1 | 0 | 25 | 280 | >500 |
| T1 | 0 | 15 | 20 | 50 |
| T2 | 0 | 15 | 20 | 50 |
| T3 | 0 | 15 | 18 | 50 |
| Donor X | | | | |
| C2 | 0 | 20 | 23 | >500 |
| T4 | 0 | 5 | 10 | 40 |
| T5 | 0 | 5 | 10 | 40 |
| T6 | 0 | 5 | 10 | 40 |
| Donor Y | | | | |
| C3 | 0 | 0 | 0 | 200 |
| T7 | 0 | 0 | 0 | 25 |
| T8 | 0 | 0 | 0 | 20 |
| T9 | 0 | 0 | 0 | 20 |
| Donor Z | | | | |

As seen from the data, although there is variability in the specimen itself, the treatment meets the criteria of the invention.

Example 2

Samples of treated SAP are prepared in 600 ml beakers. A solution containing 0.9% NaCl is made, and 600 ml of solution is added to each beaker. FORESTALL in the quantity of 0.135 g is dissolved in one of the beakers, while another beaker does not contain this additive. SAP as grade HySorb P-8400 is obtained from BASF Corporation. Now, 13.5 g of SAP is added to each beaker and stirred. The swollen SAP samples are then put into a convection oven set at 110° C. and are allowed to dry for about 48 hours. After drying, the samples are allowed to equilibrate at room temperature for about 30 minutes. The samples are then crushed at a pressure of 1 psi and scraped out of the beakers. The recovered particles are then milled in a coffee grinder and placed into a plastic vial. The vials are labeled with the quantity of the treatment added to the beakers or are labeled as controls if no additives were included.

Four absorbent structures containing 4.5 g of fluff pulp from grade RAYFLOC® JLD-E, made by Rayonier Inc., and 1.5 g of SAP as prepared according to the above procedure are made. The first structure is the control, and it contains 1.5 g of the SAP labeled as the control above. The other three structures contain 1.5 g of the treated SAP as described above. In all samples, the SAP is manually mixed with the fluff pulp to gain structures with as uniform a blend as possible.

Table 2 contains the data measured from testing.

TABLE 2

| | Ammonia Concentration ppm-hour | | | | |
|---|---|---|---|---|---|
| | 8 hour reading | 24 hour reading | 32 hour reading | 48 hour reading | 72 hour reading |
| C1 | 0 | 30 | | 105 | 430 |
| T1 | 5 | 40 | | 90 | 100 |
| T2 | 5 | 30 | | 55 | 90 |
| T3 | 5 | 30 | | 55 | 95 |
| Donor X | | | | | |
| C2 | 0 | 0 | | 30 | 145 |

TABLE 2-continued

| | Ammonia Concentration ppm-hour | | | | |
|---|---|---|---|---|---|
| | 8 hour reading | 24 hour reading | 32 hour reading | 48 hour reading | 72 hour reading |
| T4 | 0 | 0 | | 10 | 25 |
| T5 | 0 | 0 | | 15 | 30 |
| T6 | 0 | 0 | | 2 | 30 |
| Donor Y | | | | | |
| C3 | 0 | 25 | 50 | 400 | |
| T7 | 0 | 20 | 25 | 45 | |
| T8 | 0 | 25 | 30 | 60 | |
| T9 | 0 | 25 | 25 | 45 | |
| Donor X | | | | | |
| C4 | 0 | 25 | 50 | >500 | |
| T10 | 0 | 25 | 25 | 45 | |
| T11 | 0 | 25 | 25 | 45 | |
| T12 | 0 | 5 | 25 | 45 | |
| Donor Y | | | | | |

As seen from the data, the treatment meets the criteria of the invention.

Example 3

Four absorbent structures containing 4.5 g of fluff pulp from grade RAYFLOC® JLD-E, made by Rayonier, and 1.5 g of SAP from grade AQUAKEEP® SA55S, made by Sumitomo Seika Chemicals Co., Ltd. (Japan), are prepared. The first structure is sprayed with 4.5 ml of water. This sample is designated as the control. Onto the other three structures, 4.5 ml of an aqueous solution containing 1% ARQUAD HTL8-MS is sprayed. ARQUAD HTL8-MS is the tradename for hydrogenated tallowalkyl(2-ethylhexyl)dimethylammonium methyl sulfate, an example of the treatment of this invention. This chemical is manufactured by Akzo Nobel Chemicals, Inc.

Table 3 contains the data measured.

TABLE 3

| | Ammonia Concentration ppm-hour | | | |
|---|---|---|---|---|
| | 8 hour reading | 24 hour reading | 32 hour reading | 48 hour reading |
| C1 | | 25 | 300 | >500 |
| T1 | | 25 | 50 | 100 |
| T2 | | 22 | 70 | 100 |
| T3 | | 20 | 40 | 50 |
| Donor X | | | | |
| C2 | 0 | 25 | 40 | 500 |
| T4 | 0 | 12 | 15 | 40 |
| T5 | 0 | 15 | 15 | 40 |
| T6 | 0 | 5 | 10 | 25 |
| Donor Y | | | | |
| C3 | 0 | 75 | 200 | >500 |
| T7 | 0 | 25 | 25 | 50 |
| T8 | 0 | 25 | 25 | 50 |
| T9 | 0 | 25 | 25 | 50 |
| Donor X | | | | |

As seen from the data, the treatment meets the criteria of the invention.

Example 4

Four absorbent structures containing 4.5 g of fluff pulp from grade RAYFLOC® JLD-E, made by Rayonier, and 1.5 g of SAP from grade AQUAKEEP® SA55S, made by Sumitomo Seika Chemicals Co., Ltd. (Japan), are prepared. The first structure is sprayed with 4.5 ml of water. This sample is designated as the control. Onto the other three structures, 4.5 ml of an aqueous solution containing 1% ethylbis(hydroxyethyl)tallowalkyl ammonium ethyl sulfate is sprayed. Ethylbis(hydroxyethyl)tallowalkyl ammonium ethyl sulfate is an example of the treatment of this invention.

Table 4 contains the data measured.

TABLE 4

| | Ammonia Concentration ppm-hour | | | |
|---|---|---|---|---|
| | 8 hour reading | 24 hour reading | 32 hour reading | 48 hour reading |
| C1 | 0 | 35 | 100 | >500 |
| T1 | 0 | 0 | 10 | 25 |
| T2 | 0 | 0 | 0 | 0 |
| T3 | 0 | 0 | 0 | 30 |
| Donor Z | | | | |
| C2 | 0 | 30 | | >500 |
| T4 | 0 | 10 | | 30 |
| T5 | 0 | 5 | | 25 |
| T6 | 0 | 10 | | 30 |
| Donor X | | | | |

As seen from the data, the treatment meets the criteria of the invention.

Example 5

Four absorbent structures are made according to Example 4, except onto three structures, 4.5 ml of an aqueous solution containing 1% 1-propanaminium, 3-amino-N-ethyl-N,N-dimethyl-N-soya acyl derivative, ethyl sulfate is sprayed. 1-propanaminium, 3-amino-N-ethyl-N,N-dimethyl-N-soya acyl derivative, ethyl sulfate is an example of the treatment of this invention. This chemical is manufactured by Lanaetex Products, Inc.

Table 5 contains the data measured.

TABLE 5

| | Ammonia Concentration ppm-hour | | | | | |
|---|---|---|---|---|---|---|
| | 8 hour reading | 24 hour reading | 32 hour reading | 48 hour reading | 56 hour reading | 72 hour reading |
| C1 | 0 | 10 | 25 | 290 | 500 | |
| T1 | 0 | 0 | 5 | 20 | 25 | |
| T2 | 0 | 0 | 0 | 20 | 25 | |
| T3 | 0 | 0 | 5 | 25 | 25 | |
| Donor Y | | | | | | |
| C2 | 0 | 0 | 0 | 30 | | 195 |
| T4 | 0 | 0 | 0 | 0 | | 0 |
| T5 | 0 | 0 | 0 | 0 | | 0 |
| T6 | 0 | 0 | 0 | 0 | | 0 |
| Donor Z | | | | | | |

As seen from the data, the treatment meets the criteria of the invention.

Example 6

Four absorbent structures are made according to Example 4 except onto three structures, 4.5 ml of an aqueous solution containing 1% MERQUAT 550 is sprayed. MERQUAT 550 is the tradename for dimethyl diallyl ammonium chloride. Because this material does not have at least two oxygen atoms as part of the anionic portion of the salt and because this material does not have a $C_{16}$-$C_{21}$ alkyl chain as part of its structure, it is a quaternary ammonium salt that would not be an example of the treatment of this invention. This chemical is manufactured by Nalco Company.

Table 6 contains the data measured.

TABLE 6

| | Ammonia Concentration ppm-hour | | | | |
|---|---|---|---|---|---|
| | 24 hour reading | 32 hour reading | 48 hour reading | 56 hour reading | 72 hour reading |
| C1 | 25 | 30 | 80 | 100 | >500 |
| T1 | 25 | 25 | 125 | 300 | >500 |
| T2 | 25 | 25 | 100 | 225 | >500 |
| T3 | 25 | 30 | 150 | 325 | >500 |
| Donor X | | | | | |

This treatment results in inferior performance versus the preceding examples of treatments of the invention.

Example 7

Four absorbent structures are made according to Example 4 except onto three structures, 4.5 ml of an aqueous solution containing 2.5% MERQUAT PLUS 3300 is sprayed. MERQUAT PLUS 3300 is the tradename for the copolymer of dimethyl diallyl ammonium chloride, acrylic acid and acrylamide. Because this material does not have at least two oxygen atoms as part of the anionic portion of the salt and because this material does not have a $C_{16}$-$C_{21}$ alkyl chain as part of its structure, it is a quaternary ammonium salt that would not be an example of the treatment of this invention. This chemical is manufactured by Nalco Company.

Table 7 contains the data measured.

TABLE 7

| | Ammonia Concentration ppm-hour | | | | | |
|---|---|---|---|---|---|---|
| | 8 hour reading | 24 hour reading | 32 hour reading | 48 hour reading | 56 hour reading | 72 hour reading |
| C1 | 0 | 150 | 495 | | | |
| T1 | 0 | 60 | 198 | | | |
| T2 | 0 | 80 | 298 | | | |
| T3 | 0 | 120 | 398 | | | |
| Donor X | | | | | | |
| C2 | 0 | 0 | 23 | 100 | 200 | >500 |
| T4 | 0 | 0 | 10 | 50 | 100 | 300 |
| T5 | 0 | 0 | 10 | 60 | 100 | 280 |
| T6 | 0 | 0 | 10 | 50 | 95 | 280 |
| Donor Y | | | | | | |

Although this treatment results in better performance than the control, it results in inferior performance versus the preceding examples of the invention, especially considering the higher concentration of treatment.

Example 8

Four absorbent structures are made according to Example 4 except onto three structures, 4.5 ml of an aqueous solution containing 1% M-Quat Dimer 18 is sprayed. To dissolve the additive in water, the temperature needed to be raised to about 45-60° C. M-Quat Dimer 18 is the tradename for 2-hydroxypropylene-bis-1,3-(dimethylstearylammonium chloride). Because this material does not have at least two oxygen atoms as part of the anionic portion of the salt and because this material is not water soluble at 37° C., it is a quaternary ammonium salt that would not be an example of the treatment of this invention. This chemical is manufactured by BASF Corporation.

Table 8 contains the data measured.

TABLE 8

| | Ammonia Concentration ppm-hour | | | | | |
|---|---|---|---|---|---|---|
| | 8 hour reading | 24 hour reading | 32 hour reading | 48 hour reading | 56 hour reading | 72 hour reading |
| C1 | 0 | 23 | 25 | 175 | 398 | >500 |
| T1 | 0 | 15 | 20 | 50 | 65 | 400 |
| T2 | 0 | 23 | 23 | 50 | 80 | 425 |
| T3 | 0 | 15 | 23 | 50 | 98 | 400 |
| Donor X | | | | | | |
| C2 | 0 | 0 | 12 | 100 | 200 | >500 |
| T4 | 0 | 0 | 12 | 25 | 40 | 250 |
| T5 | 0 | 0 | 12 | 25 | 50 | 470 |
| T6 | 0 | 0 | 12 | 30 | 50 | 280 |
| Donor Y | | | | | | |

Although this treatment results in better performance than the control, it results in inferior performance versus the preceding examples of the invention.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of preparing an absorbent article comprising a superabsorbent power (SAP), the method comprising treating the SAP with an additive in an amount effective to reduce the malodor of a bodily fluid later absorbed by the absorbent article, wherein the additive is a quaternary ammonium salt that is water soluble at 37° C., comprises a $C_{16}$-$C_{21}$ chain, and contains at least two oxygen atoms in the anionic portion of the salt, the additive comprising 0.001-10 wt. % of an absorbent portion of the article, wherein the additive has Formula I

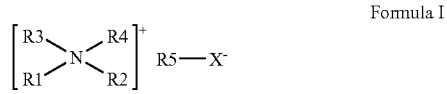

Formula I wherein R1, R2, R3, R4 and R5 are independently a straight or branched $C_1$-$C_{21}$ alkyl, alkenyl, alkynyl, haloalkyl, alkylaryl, arylalkyl, alkoxy, alkoxyalkyl, dialkylamino, dialkylamido, alkylthio, (polyalkyl)aryl, cycloalkyl or an N- or O-containing ring, optionally further comprising an N, O or S, wherein one of R1, R2, R3 or R4 comprises an alkyl $C_{16}$-$C_{21}$ chain, wherein the moiety having the alkyl $C_{16}$-$C_{21}$ chain is a mixture of alkyl $C_{16}$ and $C_{18}$ chains, wherein any two of R1, R2, R3 or R4 may be joined to form a ring, wherein X is $OSO_3$, ONO, $OCO_2$ or COO, and wherein the absorbent article is a diaper, incontinence pad, pantiliner, sanitary napkin, wipe or perspiration pad.

2. The method of claim 1, wherein the absorbent article is washable and capable of retaining the compound when the compound is added to the absorbent article after washing.

3. The method of claim 1, wherein the absorbent article is disposable.

4. The method of claim 1, wherein the additive has a formula selected from the group consisting of

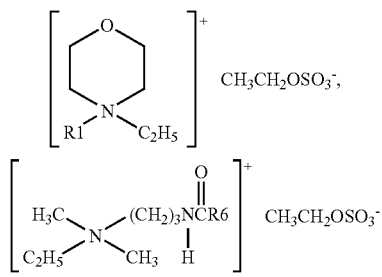

wherein R6 comprises an alkyl $C_{16}$-$C_{21}$ chain,

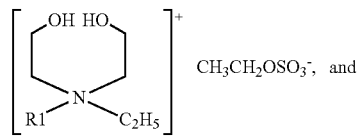

-continued

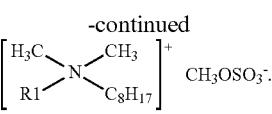

5. The method of claim 4, wherein R1 or R6 is a mixture of alkyl $C_{16}$ and $C_{18}$ chains.

6. The method of claim 1, wherein the additive has the formula

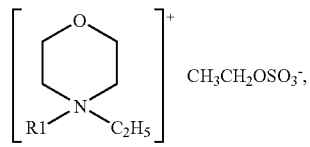

wherein R1 is a mixture of alkyl $C_{16}$ and $C_{18}$ chains.

7. The method of claim 1, further comprising addition to the article of at least one additional compound that reduces odors.

8. The method of claim 7, wherein the at least one additional compound is selected from the group consisting of an acid, a fragrance, an adsorbent, a chelating agent, and an antimicrobial.

9. The method of claim 7, wherein the compound is selected from the group consisting of a molecular sieve, silica, activated charcoal, sodium bicarbonate, and disodium EDTA.

* * * * *